United States Patent [19]

Craig

[11] Plant 4,372

[45] Jan. 30, 1979

[54] APPLE TREE

[76] Inventor: Donald E. Craig, P.O. Box 1416, Chelan, Wash. 98816

[21] Appl. No.: 879,873

[22] Filed: Feb. 21, 1978

[51] Int. Cl.[2] ..... A01H 5/03

[52] U.S. Cl. ..... Plt./35

[58] Field of Search ..... Plt./35

*Primary Examiner*—Robert E. Bagwill

*Attorney, Agent, or Firm*—Eugene D. Farley

[57] ABSTRACT

The subject apple tree comprises a new Red Delicious variety originating as a sport limb on an Oregon Spur variety tree, U.S. Plant Pat. No. 2,816. The new variety is of the spur type. Its fruit colors approximately two weeks earlier and ripens approximately one week earlier than does the fruit of its parent.

1 Drawing Figure

DESCRIPTION

The presently described new and distinct variety of apple tree was discovered as a sport limb mutation growing on an Oregon Spur variety Delicious Apple tree (U.S. Plant Pat. No. 2,816) in my cultivated apple orchard in Chelan, Wash. It has been reproduced to the third generation by budding and grafting in the aforementioned orchard and has thereby been proven to be a new and distinct variety.

The second and third generation trees have been grown for purposes of comparison alongside trees of the aforementioned Oregon Spur variety, and the Bisbee Delicious variety (U.S. Plant Pat. No. 1,565). This new variety has characteristics nearest resembling those of its parent, Oregon Spur, except that its fruit starts coloring from ten to fourteen days earlier than that of its parent and is brightly colored about 124 days after bloom. It also ripens approximately one week earlier than does the fruit of its parent.

The tree growth resembles the spur type growth of Oregon Spur. The tree is vigorous with desirable wide crotch angles.

The predominant distinguishing characteristic of my new variety as compared with Bisbee, Wellspur, Ryan (unpatented), House (unpatented) and other spur-type Red Delicious trees is that apples of my new variety start coloring with a striped formation and when a finished color is attained the striped formation is still clearly visible as lighter areas underlying the deep and intense overall red color. It differs principally from Cooper and Woods in that its fruit starts coloring about fifteen days ahead of Cooper and from twenty five to twenty nine days ahead of Woods. Also, it becomes darker red with a heavier and more predominant stripe formation than either Cooper or Woods.

The accompanying drawing comprises a color photograph of the fruit of my new variety in side view as it appears on the limb.

Fruit of my new variety is generally uniform in size averaging approximately three inches in axial diameter and three and one-sixteenth inches in transverse diameter. Cavity is symmetrical, approximately one-half inch deep by one and three-sixteenth inches broad. Calyx is closed. Skin is smooth, medium thick, and similar to Brauns (U.S. Plant Pat. No. 1,411).

Having thus described this new and distinct variety of apple tree, I claim:

1. The new and distinct variety of apple tree characterized particularly, as contrasted with its parent Oregon Spur, by the ten to fourteen day earlier coloring of its fruit; by the approximately one week earlier ripening of its fruit; and by the stripes of light color underlying the deep and intense overall red color of its fully ripened fruit, substantially as shown and described.

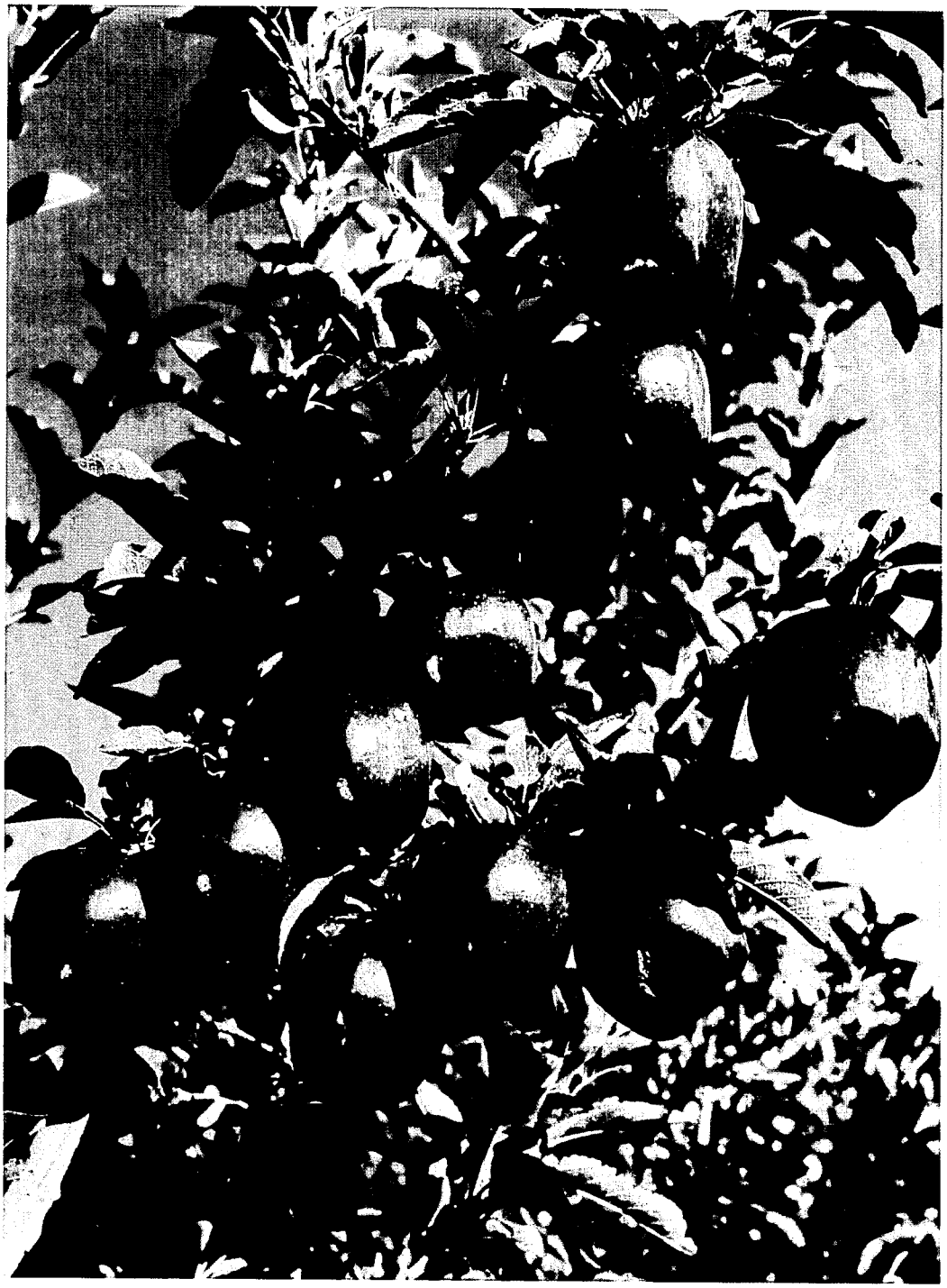

* * * * *